(12) United States Patent
Del Busto Ortega

(10) Patent No.: US 7,597,554 B2
(45) Date of Patent: Oct. 6, 2009

(54) DEVICE FOR UNILATERAL OR BILATERAL ILLUMINATION OF ORAL CAVITY

(76) Inventor: Enrique Fernandez Del Busto Ortega, Tajin 445, Apt. 9, 03020 Mexico City, D.F. (MX)

( * ) Notice: Subject to any disclaimer, the term of this patent is extended or adjusted under 35 U.S.C. 154(b) by 0 days.

(21) Appl. No.: 11/598,897

(22) Filed: Nov. 14, 2006

(65) Prior Publication Data

US 2008/0113312 A1 May 15, 2008

(51) Int. Cl.
*A61C 1/00* (2006.01)
*A61C 5/00* (2006.01)
(52) U.S. Cl. .......................................... 433/29; 433/140
(58) Field of Classification Search .................. 433/29, 433/140
See application file for complete search history.

(56) References Cited

U.S. PATENT DOCUMENTS

| | | | | | |
|---|---|---|---|---|---|
| 2,840,070 | A | * | 6/1958 | Tofflemire | ................ 600/246 |
| 3,491,971 | A | * | 1/1970 | Fisher | ........................ 248/65 |
| 4,592,344 | A | * | 6/1986 | Scheer | ...................... 600/242 |
| 5,267,857 | A | * | 12/1993 | Sickler | ........................ 433/29 |
| 5,669,769 | A | * | 9/1997 | Disel | .......................... 433/29 |
| 6,880,954 | B2 | * | 4/2005 | Ollett et al. | ................ 362/245 |
| 7,094,054 | B2 | * | 8/2006 | Cao | ............................ 433/29 |
| 2005/0239018 | A1 | * | 10/2005 | Green et al. | ................ 433/140 |
| 2006/0166161 | A1 | * | 7/2006 | Rose et al. | .................... 433/29 |

* cited by examiner

*Primary Examiner*—John J Wilson
*Assistant Examiner*—Heidi M Eide
(74) *Attorney, Agent, or Firm*—Hoffmann & Baron, LLP

(57) ABSTRACT

A device is disclosed to unilaterally or bilaterally illuminate the oral cavity that is useful for commercial cheek retractors. The present invention also discloses a bite block designed to implement the device for lateral illumination of the oral cavity.

2 Claims, 11 Drawing Sheets

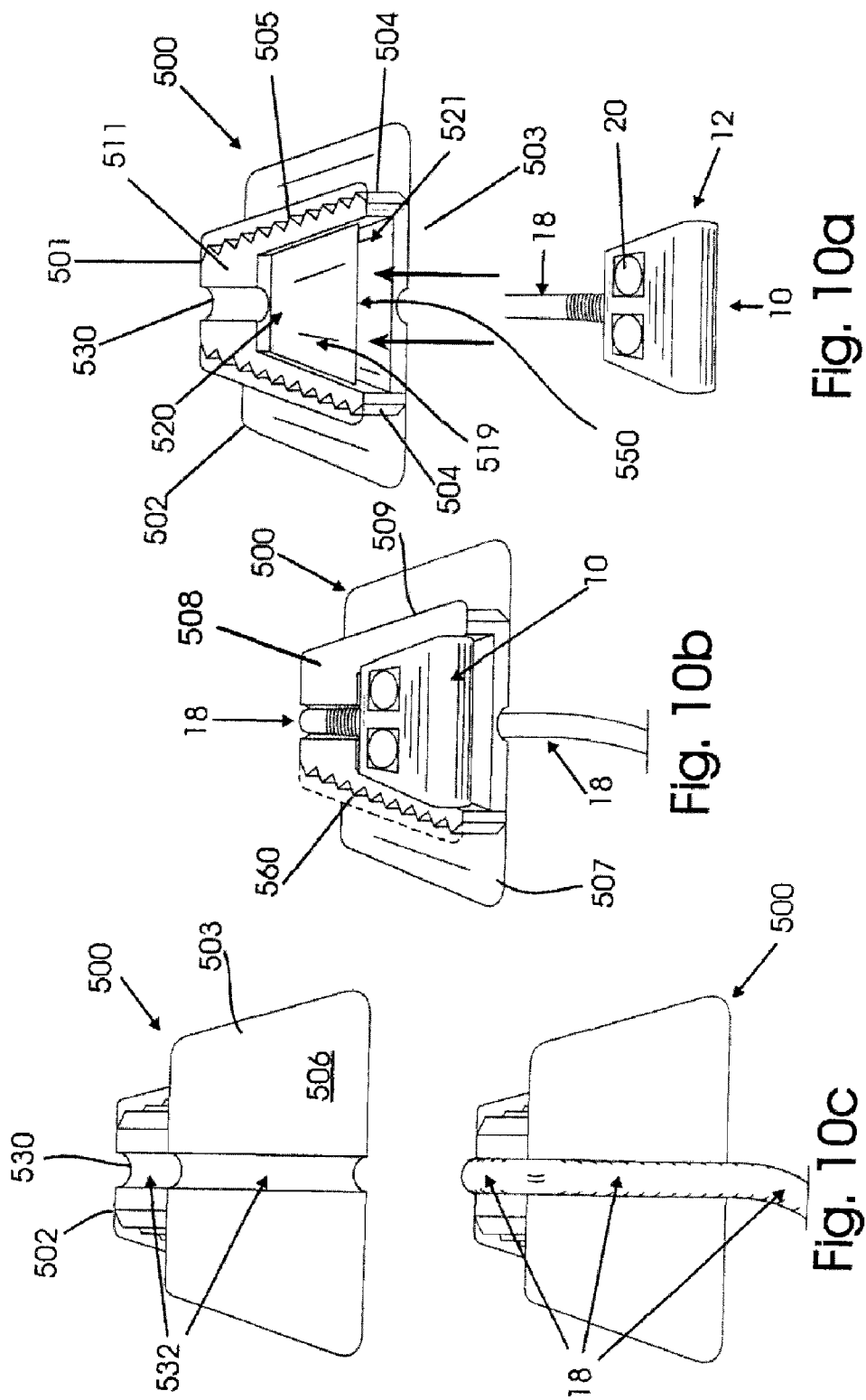

DEVICE FOR UNILATERAL OR BILATERAL ILLUMINATION OF ORAL CAVITY

FIELD OF THE INVENTION

The present invention is related to a device to illuminate the oral cavity, and more specifically, to a device for unilateral or bilateral illumination of the oral cavity that is useful for commercial cheek retractors. The present invention is also related to a bite block designed to implement the device for lateral illumination of the oral cavity.

BACKGROUND OF THE INVENTION

An important factor during dental examinations or procedures is proper illumination inside the patient's oral cavity. Proper illumination of the oral cavity is difficult to achieve for such varied reasons as, for example, the opening of the patient's mouth is reduced, the dentist is placed between the light and the patient's mouth, and the dentist also introduces his or her hand with the instruments to carry out the treatments and examinations.

Conventionally, the patient's oral cavity is illuminated by means of a light located above the dental chair, which is located approximately 1 m from the patient's back. The source of light is focused toward the patient's mouth, but most of the illumination provided is wasted because the dentist, in being very close to the patient's buccal cavity, blocks a great part of the light emitted with his or her head. Another part of the illumination is also blocked by the dentist's hand that manipulates the instruments and by the instruments themselves, thus generating many shadows and thereby greatly limiting the amount of light that can arrive in the interior of the patient's mouth. An additional factor leading to poor illumination of the oral cavity resides in the morphological factor of the buccal cavity, given which it is impossible to obtain proper illumination unless the dentist and the patient adopt very uncomfortable positions for long periods with the objective of allowing the passage of light and thus obtaining proper illumination. The solution to these problems of blocking the source of illumination consists of devising a way to place the source of illumination inside the oral cavity with the objective of eliminating this series of shadows.

Several ways to solve the problem of blocking the illumination can be found in the state of the technology. For example, U.S. Pat. Nos. 1,122,086; 1,094,575; 2,201,331; 1,998,374; 2,528,458; 2,800,896; and 3,171,203 disclose systems of illumination that solve the problem of blocking the illumination, but at the same time, present such new inconveniences as, for example, being voluminous and using focused incandescence, which generates a great deal of heat.

One technology that focused on solving the problem of heat-generation and providing a solution to the problem of intraoral illumination concerns the use of fiber optics. In general, systems of illumination by means of fiber optics have the same principle and consequently, possess the same defects. As is known by a person skilled in the art, a system of illumination by means of fiber optics is basically made up of a light source and one or more optical fibers. The light source requires high energy consumption to generate sufficient intensity and because of this, generates a great amount of heat and thus needs a cooling system. This makes the light source a voluminous and annoying apparatus.

Optical fiber is a coherent light-conducting material that presents great longitude, but with a small cross section, and this means that the light source can be far from the work area and that a certain quantity of light can transported by means of the fiber to the workspace. Although optical fibers are efficient in the conduction of light, their greatest inconvenience resides in the fact that they are very fragile and break easily. Another inconvenience is that optical fiber presents an attenuation coefficient that rises if the fiber is bent, meaning that the fibers should present large radii of curvature, and this inhibits their manipulation. That is, if a fiber bends too much, the attenuation of the conducted light will become significant, and as a consequence, reduce the intensity of the conducted light. A further disadvantage that optical fibers exhibit is their small cross section, which produces a limited field of illumination, without mentioning the difficulty in splicing these fibers. In addition to the expensive equipment and special facilities that the implementation of fiber optic technology requires, there is [also] inconvenience in handling, and the fibers tend to deteriorate with cycles of sterilization.

Examples of the first fiber optic illumination systems adapted for dental instruments are described in U.S. Pat. Nos. 3,590,232; 3,614,415; 3,616,792; 3,638,013; 3,758,951 and 5,281,134.

Examples of fiber optic illumination systems included as part of dental instruments are disclosed in, for example, U.S. Pat. Nos. 2,359,828; 3,397,457; 3,614,414; 3,634,938; 4,233,649; 4,629,425; 4,992,047; 5,457,611; 5,462,435; 5,512,686. All these designs of instruments with fiber optic illumination systems are limited to the illumination of a small area of the oral cavity and they have the disadvantages mentioned previously for the use of fiber optics.

U.S. Pat. No. 5,931,670 describes a saliva extractor illuminated by fiber optic means that includes a diffuser provided in the tip of the extractor wherein the illumination system presents the disadvantages attending the use of fiber optics.

The publication of United States of America Patent Series Application No. 2005/0227133 A1 describes a combination of lip retractor and saliva extractor in which a fiber optic illumination system can be incorporated, with the inconveniences involved in the use of this fiber optic technology.

U.S. Pat. Nos. 3,916,880 and 4,592,344, both of Schroer, describe a lip retractor that comprises a fiber optic illumination system located in both corners of the oral cavity. The lip retractor with illumination system disclosed by Schroer can provide general illumination of the oral cavity, but it has the disadvantages mentioned of fiber optics and it requires, moreover, structures especially designed to house the fiber optics.

In U.S. Pat. Nos. 6,022,214; 6,338,627; 6,575,746; and 6,908,308; all granted to Hirsch et al., an intraoral illumination device is disclosed that comprises a bite block and a light-dispersing piece connected to the bite block. The device also includes a tongue and cheek retractor, as well as channels of fluid evacuation. The light-dispersing piece provides illumination to the greater part of the oral cavity. The device presents the inconvenience of being voluminous and of complex construction, because of which, part of the arch is hidden beneath the bite block and that area cannot be reviewed or examined. Moreover, because the illumination used in this device is provided by means of fiber optics, the device possesses the disadvantages inherent to the use of fiber optics.

U.S. Pat. No. 4,872,837 discloses a surgical or dental instrument capable of providing illumination. The instrument includes, among other parts, a stem of transparent material intended to aspirate, clean, dry off and illuminate, wherein the wall of the stem is used as a conductive means of light. Nevertheless, this instrument has the inconvenience that the area of illumination is very limited.

U.S. Pat. No. 6,332,776 discloses a bite block that makes use of a reflected light source of optic or internal fiber to illuminate the mouth, and the publication of United States of America Patent Application No. 2005/0239017 is related to another bite block design in ring form that is used as a diffuser of microfluorescent light; however, both bite block designs hide part of the patient's arch and therefore, make the review and examination of these areas impossible.

U.S. Pat. Nos. 4,643,172 and 4,807,599 describe illuminating tongue depressors that comprise a means to concentrate and direct the light where said means is used as a diffuser that would be very useful for a review procedure since only a defined area of the mouth is illuminated, and therefore, it is not capable of illuminating the intraoral cavity for a treatment since it requires holding the tongue depressor while the dentist is working, which means the assistant loses a hand that could be used to help the dentist.

In U.S. Pat. No. 6,607,384, Nakanishi describes an illumination device to be used with a dental or medical instrument for treatment of a site. The illumination device includes a series of light-emitting diodes (LED) provided in a hoop-shaped LED holder that is placed in the distal part of the dental instrument such as, for example a drill. The illumination device is mounted on the drill by means of grips that clasp the neck of the drill in a such way that this passes through the holder where the LEDs are located in the periphery of the drill. When the LEDs emit light, this light is irradiated from the distal end of the drill in all directions, avoiding shadows in the same. This illumination device is excellent when preparing a cavity, but because the light is mounted on the instrument, when the instrument is withdrawn from the mouth, the dentist will be without light and when working with another instrument that does not have this illumination device, he or she will continue working under the usual (faulty) conditions of illumination Nakanishi suggests that this illumination device can be mounted on any instrument; most of the instruments in a dental clinic are for straight work (98%); that is, the working tip of the instrument corresponds to the axial axis of the dentist's hand (that is, the axial axis of the hand and the working direction of the instrument are parallel). The remaining 2% of instruments include the high-speed handpiece and the low-speed contra-angle ("two instruments") that are for angled work, that is, the working tip of the instrument forms an angle with respect to the axial axis of the dentist's hand (that is, the working direction of the instrument is perpendicular to the axial axis of the dentist's hand). Nevertheless, the direction of the light provided by Nakanishi's illumination device is parallel to the direction of the attachment grips that clasp the neck of the instrument, and this implies that when the illumination device is placed on an instrument, the direction of the light will be perpendicular to it. It is thus impossible to work with this addition placed on a straight instrument. Therefore, the device disclosed by Nakanishi can only be placed on 2% of the instruments, since 98% of instruments are straight, and because of this, the device does not satisfy 100% of the need for illumination of the intraoral cavity required by the dentist.

An illumination device of the oral cavity provided in a bite block that consists of light-emitting diodes (LED), is described in U.S. Pat. No. 6,830,451 and in the publication of United States of America Patent Application No. US2005/0239018. As described, the illumination in the bite block is provided by means of a series of LEDs provided on the lateral or lingual face of the bite block in such a way that the light is emitted laterally. The illumination provided by this device lights the upper and right inferior quadrants from the left side and vice versa. The feed source for the illumination device is by means of batteries that are contained inside the bite block. This type of device presents some inconveniences, such as, for example, when emitting the light laterally what is illuminated is really the lingual faces of the teeth opposite, but the occlusal faces would be moderately illuminated, while the vestibular faces would not be illuminated. Thus, it is impossible for this illumination device to be useful in illuminating the interior of the preparation of a tooth. Another inconvenience in the illumination device of U.S. Pat. No. 6,830,451 and publication US2005/0239018, resides in the necessity that the patient have the entirety of his or her back dental pieces, upper as well as lower, because this device cannot be used in a patient who lacks molars, either upper or lower, as the device rests on their occlusal faces.

The publication of the United States of America Patent Application No. US2004/0063060 describes an illumination device of the oral cavity, which is placed on the molars to provide illumination in the interior. The device includes a battery, a band, a light source and a means to secure the device to the molars with temporary cement, or to anchor to brackets, or to an orthodontic band that is in itself an inconvenience.

In accordance with the foregoing, a necessity exists in the state of the technology for an illumination device of the intraoral cavity that provides efficient illumination of the entirety of the oral cavity. An additional necessity exists for an illumination device of the oral cavity that does not get in the way of work and that allows any type of treatment to be carried out without respect to the instruments being used or where they are used. Yet another necessity exists in the state of the technology for an illumination device of the oral cavity that is not complicated to install and is reasonable in cost. For these reasons, an object of the present invention is to provide a device for illumination of the oral cavity that is economical and easily managed, and that does not require special structures and facilities.

Another object of the present invention is to provide a device for illumination of the oral cavity that efficiently illuminates the lingual, occlusal and vestibular faces.

Yet another object of the present invention consists of providing a device for illumination of the oral cavity that can be placed in a commercial cheek retractor.

A further object of the present invention is to provide a device for unilateral or bilateral illumination of the oral cavity so that the dentist can obtain total or partial illumination.

An additional object of the present invention is to provide a device for illuminating the oral cavity that allows the dentist to regulate the intensity of the illumination in each upper and lower quadrant independently.

A further object of the present invention is to provide a device for unilateral or bilateral illumination of the oral cavity.

Yet another object of the present invention is to provide a novel bite block design to implement the device for lateral illumination of the oral cavity.

BRIEF DESCRIPTION OF THE INVENTION

The present invention is related to a device for unilateral or bilateral illumination of the oral cavity that comprises: light-emitting means to illuminate the oral cavity; a pair of carrying members to house the light-emitting means and hold them in fixed position; a system of illumination control to supply electric power to the light-emitting means to unilaterally or bilaterally illuminate the oral cavity, to increase and/or diminish the luminous intensity; means to connect the carrying members of the light-emitting means to the illumination control system; and a feed source regulator of electric power.

BRIEF DESCRIPTION OF THE FIGURES

The aspects that are considered characteristic of the present invention will be established with particularity in the attached claims. However, the same invention, in its organization as well as method of operation, together with other objectives and advantages of the same, will be better understood in the following description of certain embodiments, when read in connection with the drawings that accompany it, in which:

FIG. 3d is a view in cross section along line 3d-3d of FIG. 3a.

FIG. 10a shows a novel bite block for placement of the device for unilateral illumination of the oral cavity of the present invention.

FIGS. 10b and 10c show an upper and lower view of the bite block of FIG. 10a.

DETAILED DESCRIPTION OF THE PREFERRED EMBODIMENTS

Figure 1:
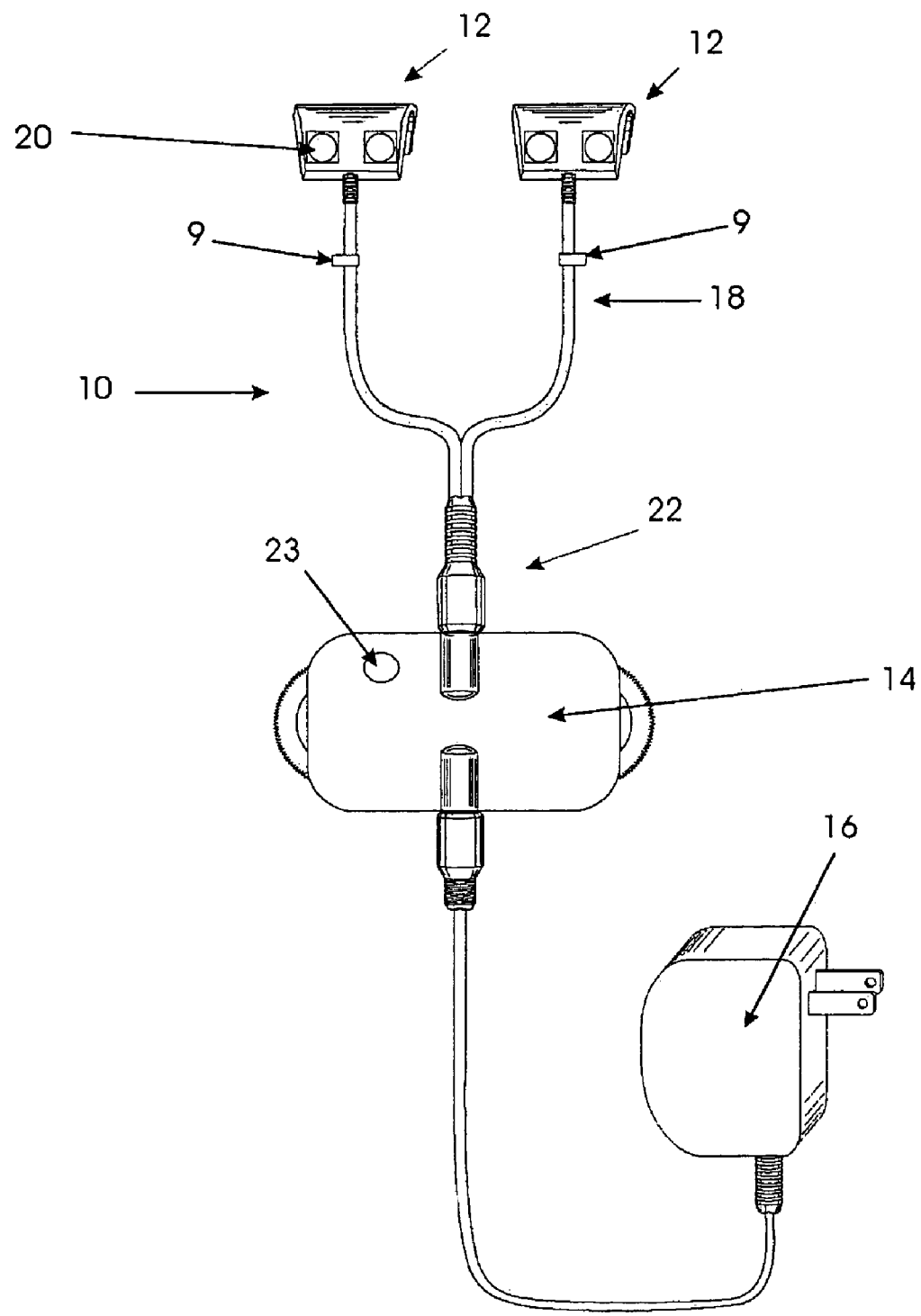
FIG. 1 is an illustration that shows the device for unilateral or bilateral illumination of the oral cavity of the present invention.
Figure 2:
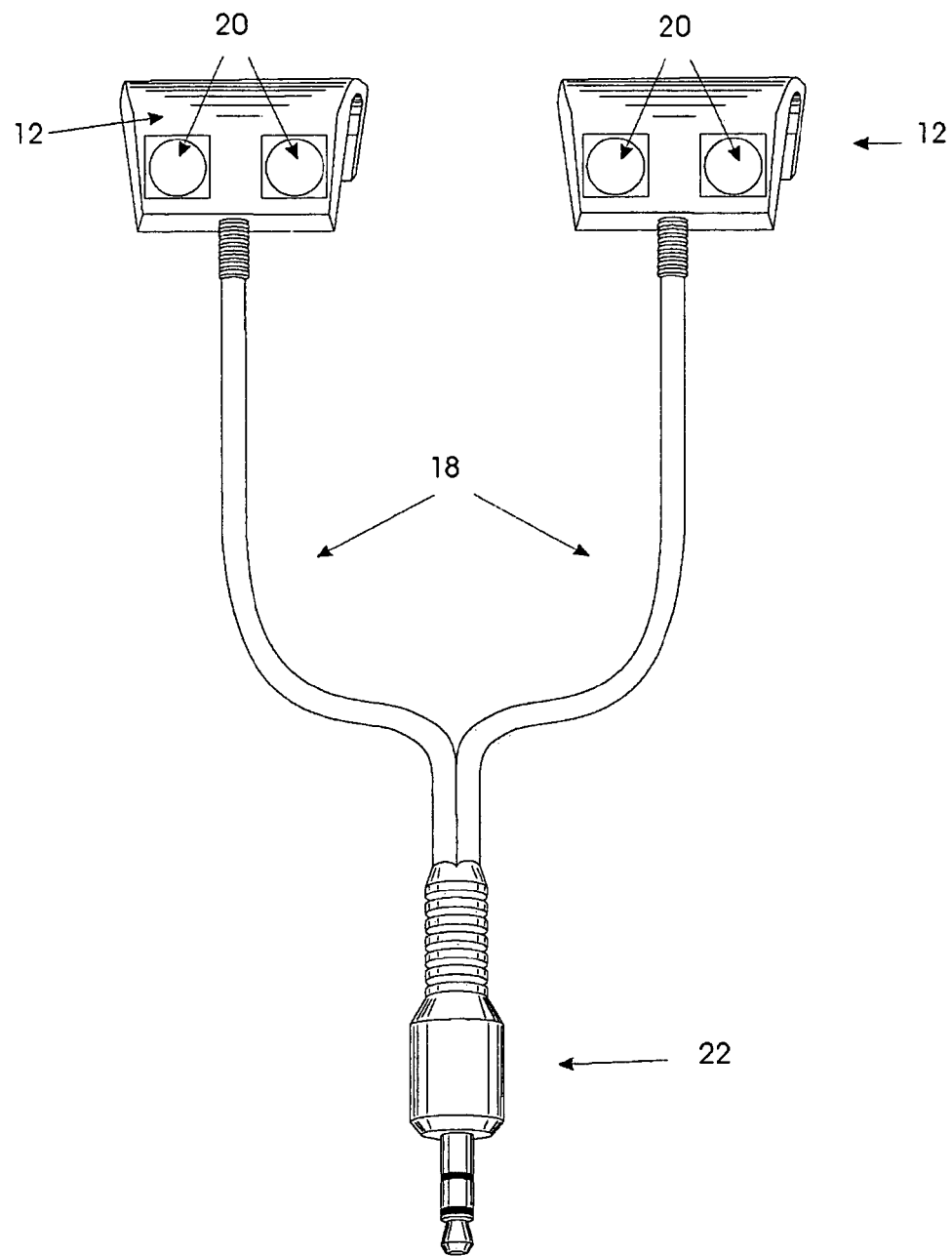
FIG. 2 is an illustration that shows the illumination member of the device for unilateral or bilateral illumination of the oral cavity of the present invention.

Making reference to FIG. 1, a device is shown there for unilateral or bilateral illumination of the oral cavity in accordance with the present invention that may be placed in a commercial cheek retractor or a novel bite block of the present invention. The device for unilateral or bilateral illumination of the oral cavity is indicated with reference numeral 10. The illumination device 10 of the present invention comprises in general a pair of carrying members of light-emitting means 12, light-emitting means 20; a system of illumination control 14, and a feed source regulator of electric power 16 (this may be a conventional suppressor that reduces the voltage of either 110 or 220 V to the voltage required by the system of illumination control 14). The carrying members of light-emitting means 12 are connected to the illumination control system 14 by means of independent cables 18 that end in a stereo-type plug connector 22 (see FIG. 2). As will be described in detail further on, the illumination control system 14 provides the electric power in a controlled way to the light-emitting means 20 to illuminate the oral cavity unilaterally or bilaterally, and/or increase or diminish the luminous intensity.

Figure 3A:
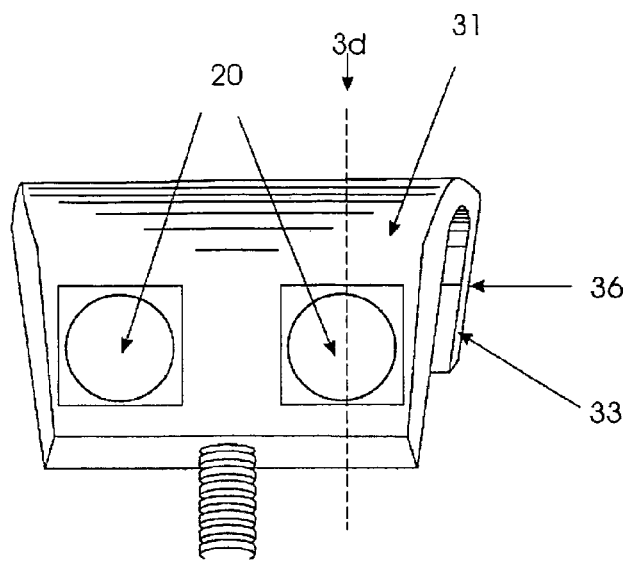
FIGS. 3a-3c are enlarged views that show in detail the configuration of a carrying member of the light-emitting means of FIGS. 1 and 2.
Figure 3B:
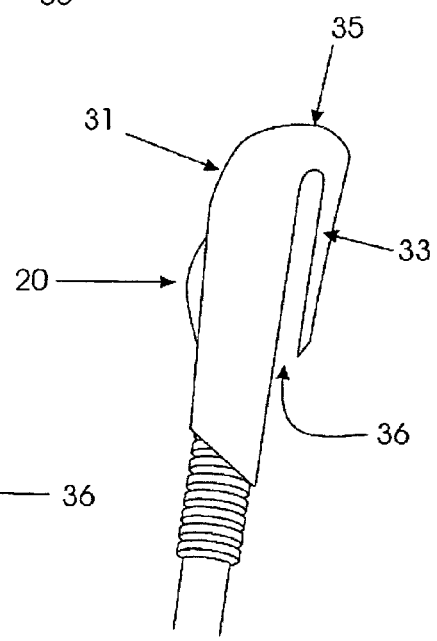
Figure 3C:
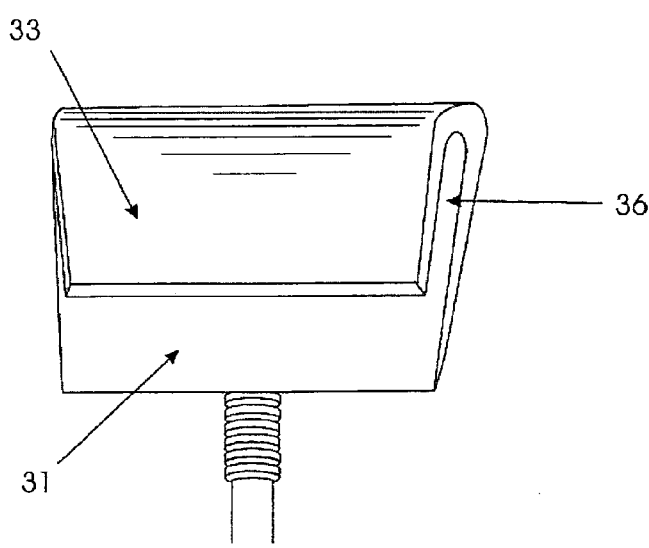

FIGS. 3a-3c are front, side and back views that show in detail the particular configuration of a carrying member of light-emitting means 12 of the invention. Preferably, each carrying member 12 is a unitary structure that serves to house and to maintain in fixed position a pair of light-emitting means 20. Preferably, the configuration of the carrying member of light-emitting means 12 is such that it allows its placement in a secure way in the inside wing of any commercially available cheek retractor, as will be described below in detail with reference to FIGS. 6a-6b, 7a-7b, 8a-8c, and 9a-9c.

The carrying member of light-emitting means 12 has a front portion 31 to house and establish the power supply of the light-emitting means 20 in this carrying member 12, a back portion 33 located so that it is separated from the front portion 31 in a parallel manner, and an upper portion 35 that unites the upper ends of front and back portions 31 and 33. In general, the inner surface of upper portion 35, in combination with the inner surfaces of front and back portions 31 and 33 form a cavity 36 to allow placement and fastening of the carrying member of light-emitting means 12 when it is mounted in the inside wing of a cheek retractor. In other words, the internal surfaces of the front 31, back 33 and upper portion 35 form a fastening member. In the embodiment illustrated in FIGS. 3a-3c, it can be seen that front portion 31 is substantially thicker than back portion 33. Typically, front portion 31 is somewhat wider than back portion 33, but both portions are equal in length.

Figure 3D:
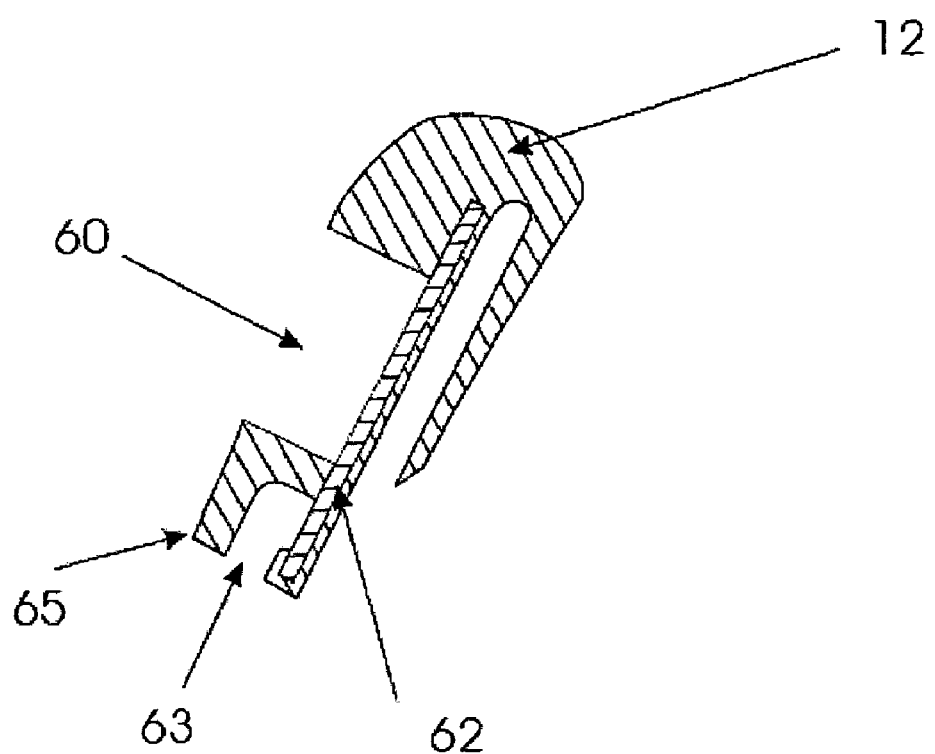

In a particularly preferred embodiment, as shown in FIG. 3d, front portion 31 of each carrying member of light-emitting means 12 also comprises two cavities 60 that are separately formed (only one is shown in FIG. 3d) to house each light-emitting means 20 in carrying member 12. Each cavity 60 is preferably of circular form and extends through most of the thickness of this front portion 31, as illustrated. Front portion 31 to house and establish the electric power supply to light-emitting means 20 also includes an electronic circuit card 62 located immediately beneath each cavity 60 and a connection conduit 63 centrally disposed in the lower part 65 of this front portion 31. Electronic circuit card 62 extends below cavity 60 toward connection conduit 63 to connect each end of electronic circuit card 62 by means of cable 18 coming from illumination control system 14, energizing said electronic circuit card 62 and as a result, this electric power is transformed into luminous energy by light-emitting means 20. For the purpose of preventing movement of light-emitting means 20 toward the outside of each cavity 60 of front portion 31 of each carrying member of light-emitting means 12, the terminals of each light-emitting means 20 are preferably welded to electronic circuit card 62 (not shown). However, other means of fixation or immobilization by pressure can be used (for example, a projection in the upper part of each cavity) to keep light-emitting means 20 in place in a removable way that allows replacement of light-emitting means 20 in case of failure.

However, it is to be understood that front portion 31 of the carrying member of light-emitting means 12 may have three or more cavities to receive the same number of light-emitting means 12.

The carrying member of light-emitting means 12 is fabricated of a thermoplastic material that allows flexion toward the outside of back portion 33 when this carrying member 12 is placed in the inside wing of the cheek retractor.

In a particularly preferred embodiment of the invention, light-emitting means 20 are light-emitting diodes (LED).

Figure 4A:
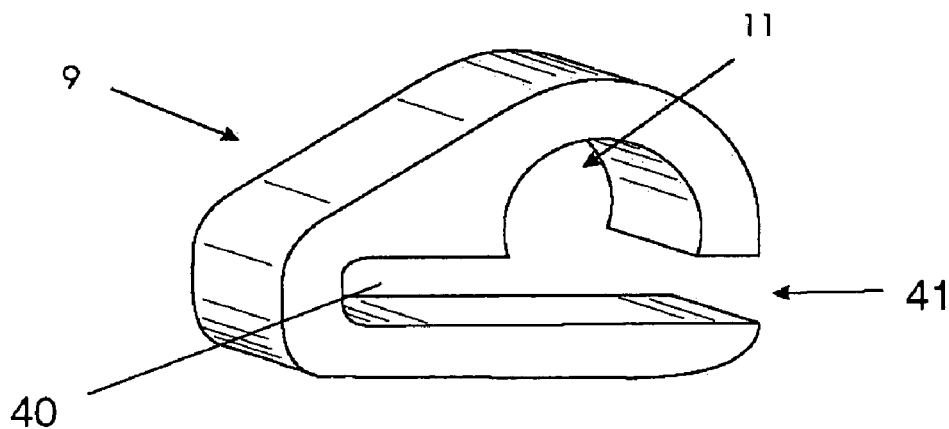
FIGS. 4a-4b are illustrations that show the holder of the illumination member's cable and its placement in a conventional cheek retractor.
Figure 4B:
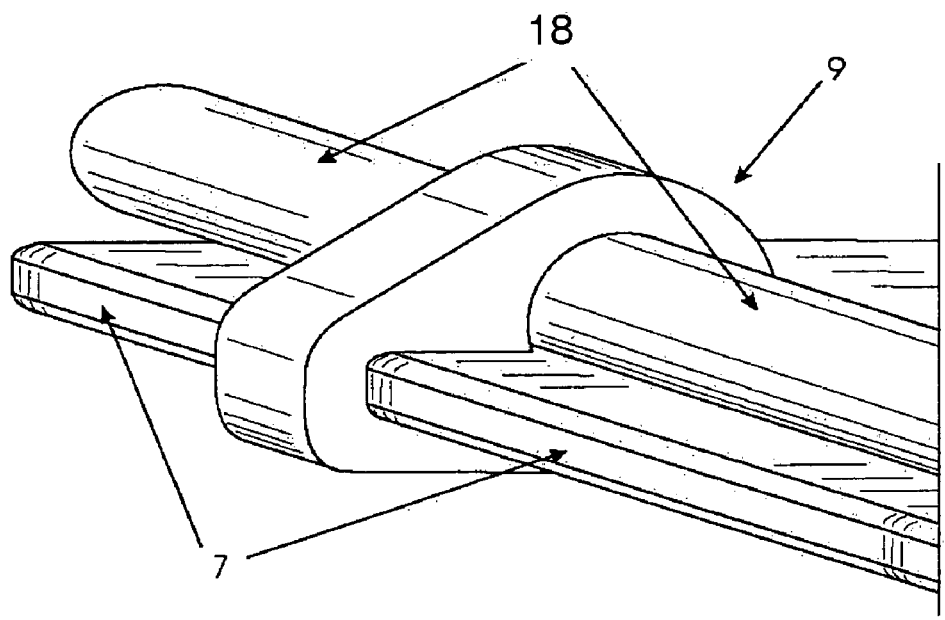

The device for unilateral or bilateral illumination of the oral cavity of the present invention also includes a pair of cable holders 9, such as, for example, a clip, as shown in FIG. 4a. Holder 9 is used to fasten cable 18 that connects carrying member 12 with illumination control system 14 to the cheek retractor (partially shown in FIG. 4b). As can be seen, the holder has a fastening portion 40 for mounting holder 9 in a fixed manner on a wall of retractor 7, a cable-fastening portion 11 in the shape of a half moon where it crosses and holds cable 18 that comes from each carrying member of light-emitting means 12, and an entry slit 41 in which the wall of the cheek retractor is inserted. In FIG. 4b one of these clips 9 is shown installed, indicating how cable 18 is held by clip 9 and cheek retractor 7 is inserted in slit 41.

Figure 5A:
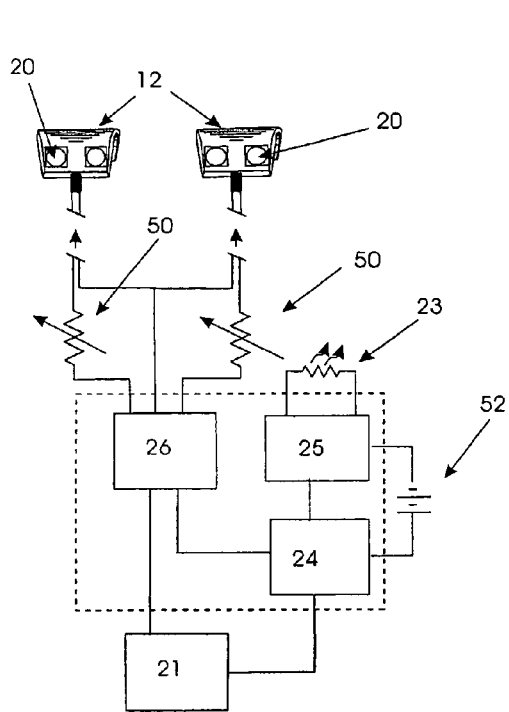
FIG. 5a is a block diagram of the illumination control system of the light-emitting means of the carrying members of the device for unilateral or bilateral illumination of the oral cavity of the present invention.

Referring now to FIG. 5a, a block diagram is shown of an embodiment of the illumination control system 14 of the device for unilateral or bilateral illumination of the oral cavity 10. The illumination control system 14 has as its function controlling the exit current that feeds to light-emitting means 20 and as a result, independently controlling the intensity of light emitted by each pair of light-emitting means 20. In the preferred embodiment, control of the intensity of illumination of each pair of light-emitting means 20 is independent and obtained by means of potentiometers 50. Each potentiometer 50 controls a corresponding pair of light-emitting means 20 such that the intensity of the light of both light-emitting means 20 can be increased, [or] the intensity of one light-emitting means 20 can be increased and/or the intensity of the other one diminished. The illumination control system 14 also includes a circuit voltage regulator 21 as a means of protection in a such a way that any kind of feed source electric power regulator 16 may be used (that is, any type of voltage suppressor). System 14 comprises one or two rechargeable batteries 52, a recharge indicator 23, and its associated recharge circuit 24 for recharging batteries 52. Recharge circuit 24 includes a charge sensor 25 so it can be connected to suppressor 16 and as soon as the batteries reach their maximum charge, the circuit is disabled. The illumination control system has a circuit 26 that works as an internal commutator in such a way that the device can be operated for the unilateral or bilateral illumination of the oral cavity of the present invention with the batteries, and if at that time the suppressor is connected, it will automatically work with the current provided by suppressor 16, and at the same time, batteries 52 will be recharged.

Figure 5C:
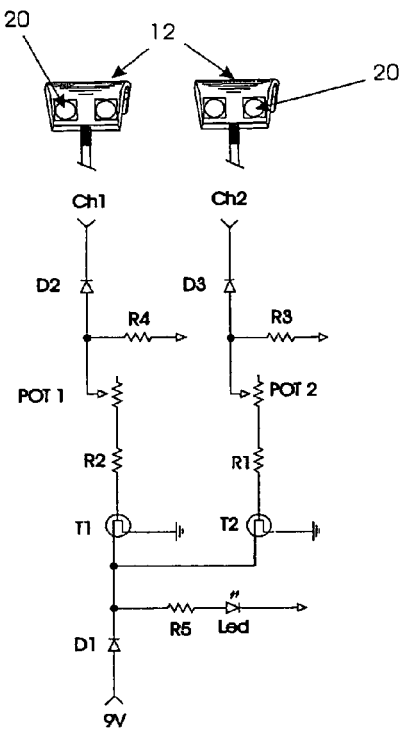
FIG. 5c shows the electronic circuit of an alternative embodiment for controlling the illumination of the device for unilateral or bilateral illumination of the oral cavity.
Figure 5B:
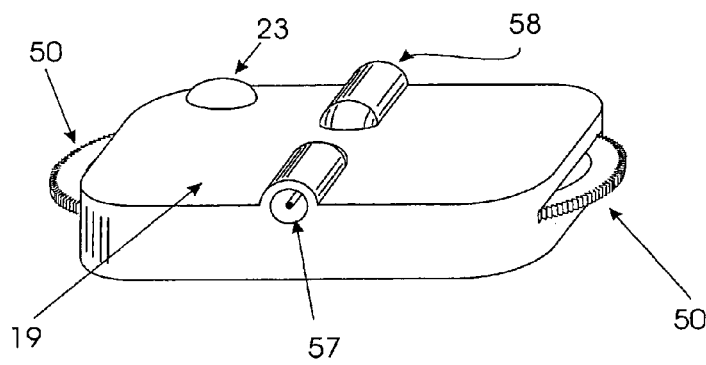
FIG. 5b is a schematic illustration that shows the illumination control system and disposition for the control of light intensity.
Figure 6A:
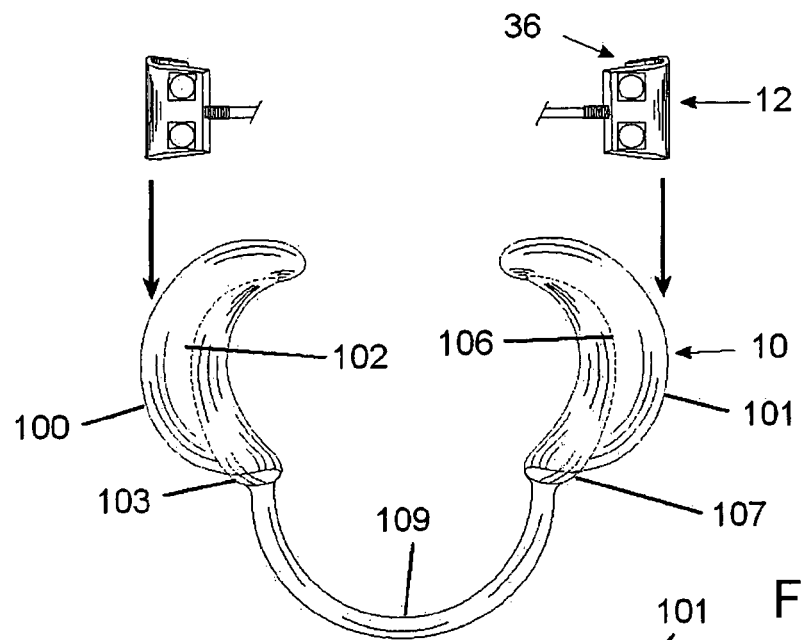
FIGS. 6a-6b are schematic illustrations that show placement of the device for unilateral or bilateral illumination of the oral cavity of the present invention in a cheek retractor of the type described in U.S. Pat. No. 4,200,089.
Figure 6B:
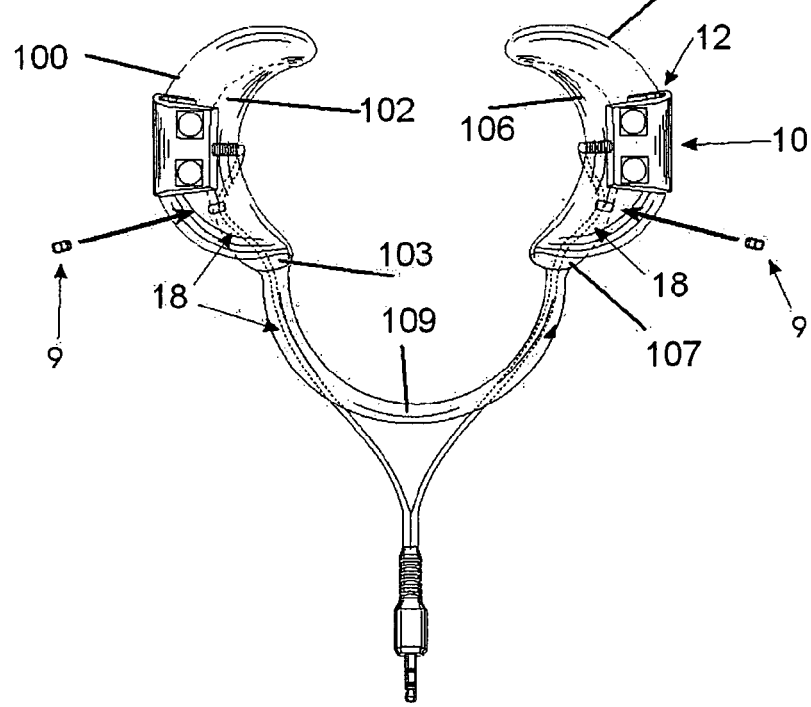
Figures 7A, 7B:
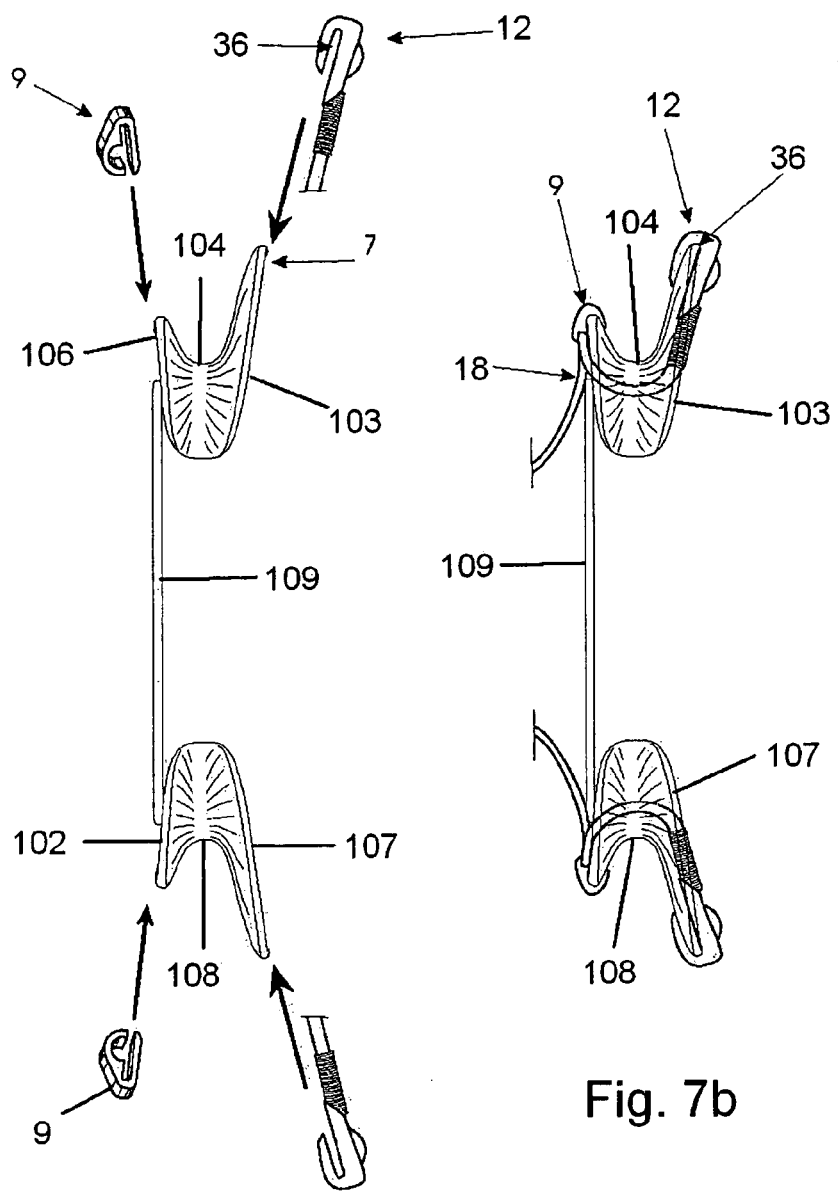
FIGS. 7a-7b are plan views from above that illustrate placement of the device of FIGS. 6a-6b for unilateral or bilateral illumination of the oral cavity of the present invention.

As may be observed, the illumination control system 14 of FIG. 5a is shown in FIG. 5b as an independent module enclosed in a housing. Illumination control system 14 has a first connection for entry of current 57 that connects feed source electric power regulator 16 to said control system 14, a second entry connection 58 of a stereo-type jack to establish the power supply connection through stereo-type plug connector 22 toward the carrying members of light-emitting means 12. In this figure, the two potentiometers 50 disposed on opposite sides of the housing of illumination control system 14 may also be observed, and a recharge batteries indicator 23 to indicate to the user the need to recharge batteries 52.

FIG. 5c shows an electronic circuit of an alternative embodiment for controlling the illumination of device 10 for unilateral or bilateral illumination of the oral cavity. The illumination control circuit 54 shown in FIG. 5c has the same function as illumination control device 14 illustrated in FIG. 5a. That is, circuit 54 controls the exit current that feeds to light-emitting means 20 and as a result, it controls the intensity of light emitted by each pair of light-emitting means 20 independently. However, the alternative embodiment of illumination control circuit 14 does not include the rechargeable batteries, recharge indicator or recharge circuit associated with recharging the batteries. Illumination control circuit 54 comprises a feed entry from 6 to 12 volts; a diode D1 that protects circuit 54 against the polarity of the feed current; a resistor R5 that reduces the feed voltage to feed a light-emitting diode that indicates that circuit 54 is receiving electricity; the feeding voltage is split to be fed to each transistor T1, T2, where each transistor regulates the entry voltage and reduces it to 5 volts; the reduced voltage is driven toward corresponding resistors R2, R1 that further reduce the voltage of 5 volts to 3 volts to avoid heating the light-emitting means 20 connected to respective channels Ch1, Ch2; the reduced voltage that leaves R2, R1 is fed to the corresponding potentiometers POT1, POT2 to regulate the exit voltage in each channel Ch1, Ch2, thus also regulating the intensity of the light of each light-emitting means 20 of illumination control circuit 14. Illumination control circuit 14 also comprises corresponding grounded resistors R4, R3 to achieve the complete turning off of each light-emitting means 20 connected to channels Ch1, Ch2, respectively; and diodes D2, D3 that serve as protection against the polarity of each channel Ch1, Ch2. Each channel Ch1, Ch2 is connected to a stereo-type jack (not shown) and they can be the illumination control circuit 54 held inside a housing similar to the one shown in FIG. 5b Making reference now to FIGS. 6a-6b and 7a-7b, an embodiment is shown for placement of the device for unilateral or bilateral illumination of the oral cavity of the present invention in a cheek retractor that has the configuration disclosed in U.S. Pat. No. 4,200,089, titled "Mouth Corner Spreader," granted to Masaomi Inoue Apr. 29, 1980, which is incorporated here by reference in its totality. Inoue's cheek retractor comprises a pair of hook structures 100 and 101 arranged opposite one another and designed to adjust to the corners of the mouth; each of hook structures 100, 101 consists of an essentially "C"-shaped outer portion 102, 106, an inner essentially "C"-shaped portion 103, 107 provided separated from outer portion 102, 106 and an arched joining portion 104, 108 that joins the outer and inner portions along the inner edges of the "C"-shaped portions. Both hook structures 100, 101 are connected by means of an elastic or spring arm 109. In the embodiment of the present invention, the device for unilateral or bilateral illumination of the oral cavity 10 is placed in the inner "C"-shaped portions 103, 107 of each hook structure 100, 101, and the cable 18 of said device 10 is held in the outer "C"-shaped portions 102, 106, by each holder 9.

Preferably, the cavity 36 of each carrying member of light-emitting means 12 is inserted in the wall of the central arched part of each internal "C"-shaped portion 103, 107, of hook structures 100, 101 of the cheek retractor in a such a way that each carrying member 12 will be in the middle front part of the cheek for its inner face to be behind the labial corner. Placement of the carrying members of light means 12, inserted in both inner portions 103, 107, is such that cable 18 of each carrying member 12 is directed toward the center of the retractor. The cable 18 of each carrying member 12 is joined by connector 22. The connector 22 is made to pass through the center of the cheek retractor so that cables 18 cross the retractor toward its outer part where each cable is held in each outer "C"-shaped portion 102, 106, respectively, of hook structures 100, 101, by means of clip 9 for adjusting and affixing said cable to the retractor in such a way that the cable circles the retractor from the inside toward the outside.

Once the clips 9 and cable 18 are placed in their positions, the cheek retractor is placed in the mouth of the patient. Connector 22 is connected to the second entry connection 58 to establish connection of the power supply from the illumination control system 14, and the feed source regulator of electric power 16 is connected to the first current entry connection 57. Once the electrical connection of carrying members 12, illumination control system 14, and feed source 16 is established, light-emitting means 20 will light and the dentist can regulate the intensity of each light-emitting means to illuminate the patient's oral cavity unilaterally or bilaterally. Moreover, once the electric current begins to flow toward illumination control system 14, charge sensor 25 of recharge circuit 24 contained in illumination control system 14 detects the level of charge of batteries 52 and instructs circuit commutator 26 to allow the flow of electricity and in the same way to recharge batteries 52 if they are discharged. In a preferred embodiment, said circuit commutator 26 allows operation of the device for unilateral or bilateral illumination of the invention only when batteries 52 are doing without the feed source regulator of electric power 16. Nevertheless, if the feed source regulator of electric power 16 is connected at that time, it will automatically work with the current that this provides, and batteries 52 will also be recharged at the same time.

Figure 8A:
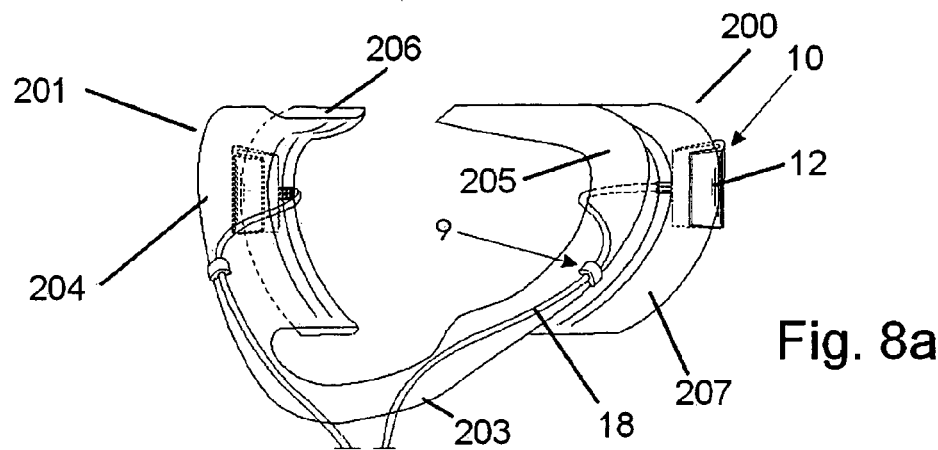
FIGS. 8a-8c are views in perspective from the front, back and above that show placement of the device for unilateral or bilateral illumination of the oral cavity of the present invention in a cheek retractor of the type described in international publication WO 02/07636 A1.
Figure 8B:
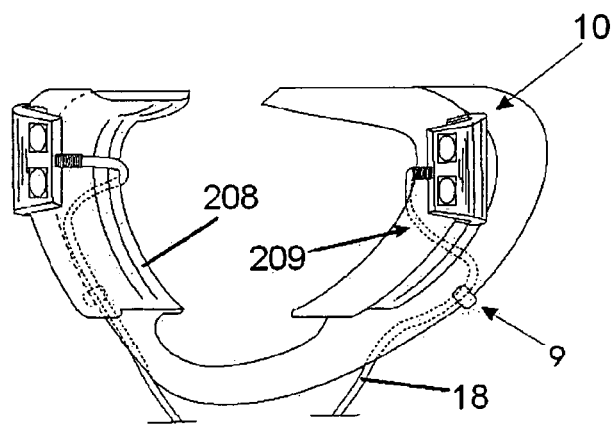
Figure 8C:
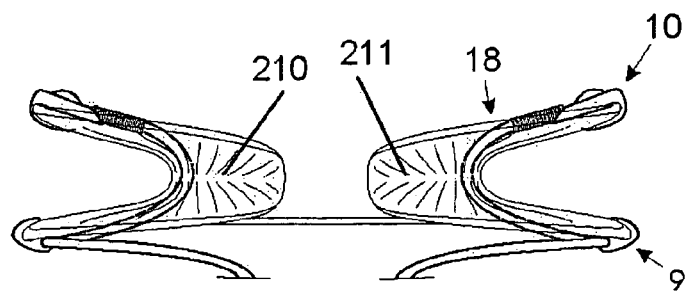

FIGS. 8a-8c show an alternative embodiment of the device for unilateral or bilateral illumination of the oral cavity of the present invention in a cheek retractor that has the configuration disclosed in International Publication WO 02/07636 A1, which is incorporated here by reference in its totality. FIG. 8a is a front view of the retractor, FIG. 8b is a back view of the retractor and FIG. 8c is a view from above. The cheek retractor of publication '7636 includes a pair of hollow arched bodies 200, 201 adapted to adjust to the lips and corners of the mouth, and to keep them behind the front teeth. Arched bodies 200, 201 are integrally connected by arched elastic arm 203 connected to the lower parts of hollow bodies 200, 201, which extends downward and is placed outside the mouth, on the front part of the lower lip, when the hollow bodies are placed in their location. Each hollow body has a channel form in cross section that includes front side walls 204, 205, and back side walls 206, 207 designed to couple with the lips and cheeks in the corners of the patient's mouth. The hollow bodies also include opposed inner surfaces 208, 209 and outer surfaces 210, 211 that extend between the front and back side walls. During use, the outer surfaces will be in direct contact with the lips and the patient's cheeks.

In the alternative embodiment of the present invention, each carrying member of light-emitting means 12 of device 10 for unilateral or bilateral illumination of the oral cavity (partially illustrated in FIGS. 8a-8c) is inserted in the back side wall 206, 207 of hollow body 201, 202, using the cavity formed by the front and back portions of this carrying member 12. Cable 18 of each carrying member 12 extends on the inner surface 208, 209 toward the front side wall 204, 205 of hollow body 201, 202, to be held and fixed to this front side wall by means of holder 9.

Once the clips 9 and cable 18 are set in position, the cheek retractor is placed in the mouth of the patient. Connector 22 is connected to second entry connection 58 to establish the power supply connection of illumination control system 14 and the feed source regulator of electric power 16 is connected to the first current entry connection 57. Once the electrical connection of carrying members 12, illumination control system 14 and feed source 16 is established, light-emitting means 20 will light and the dentist can regulate the intensity of each light-emitting means for unilateral or bilateral illumination of the patient's oral cavity. Moreover, once the electric current begins to flow toward illumination control system 14, charge sensor 25 of recharge circuit 24 contained in illumination control system 14 detects the level of charge of batteries 52 and instructs commutator 26 to allow the flow of electricity and thus recharge batteries 52 if they are discharged. In a preferred embodiment, said circuit commutator 26 allows operation of the device for unilateral or bilateral illumination of the invention only when batteries 52 are doing without the feed source regulator of electric power 16. Nevertheless, if the feed source regulator of electric power 16 is connected at that time, it will automatically work with the current that this provides, and batteries 52 will also be recharged at the same time.

Figure 9A:
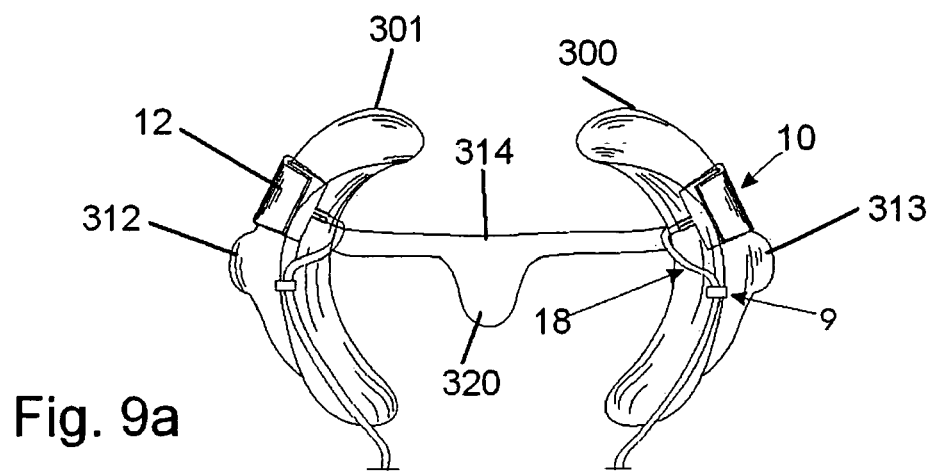
FIGS. 9a-9c are views in perspective from the front, back and above that show placement of the device for unilateral or bilateral illumination of the oral cavity of the present invention in a cheek retractor of the type described in U.S. Pat. No. 3,916,880.
Figure 9B:
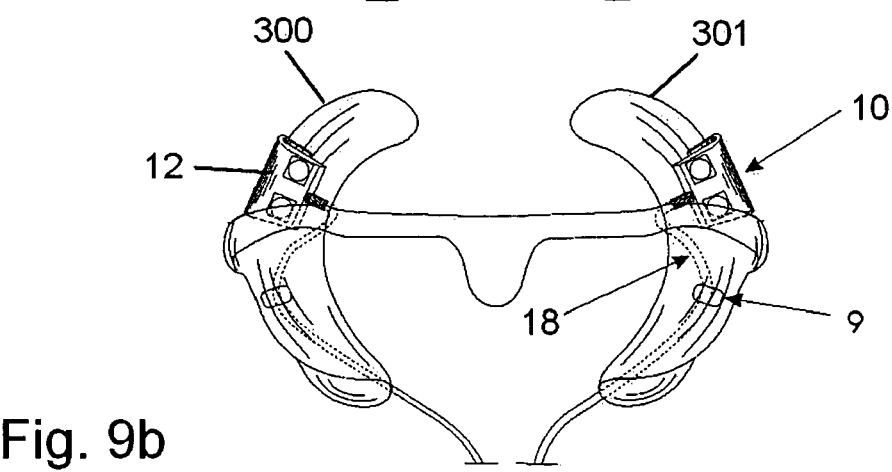
Figure 9C:
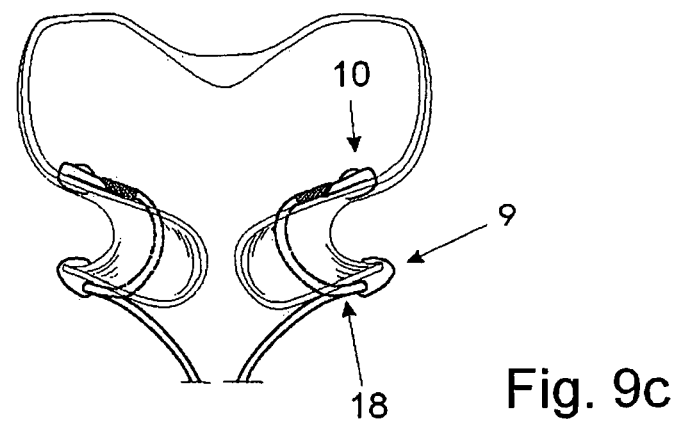

In an additional embodiment of the invention that is illustrated in FIGS. 9a-9c, the device for bilateral illumination of the oral cavity of the present invention can be used in a cheek retractor disclosed in U.S. Pat. No. 3,916,880, titled "Device for holding open the mouth" granted to Wolfgang Schroer Nov. 4, 1975, which is incorporated here by reference in its entirety. FIG. 9a is a front view of the retractor, FIG. 9b is a back view of the retractor and 9c a view from above. The cheek retractor of Schroer includes a couple of arch-shaped hollow bodies 300, 301 having a channel-shaped cross section that receive the lips and separate them. The back walls of the hollow bodies define flanges 312, 313 that are oriented toward the outside and enlarged. The extended and enlarged flanges form the ends of an essentially U-shaped stirrup 314. The stirrup 314 unites the two channels 300, 301 and includes a web (not shown) that interconnects flanges 312, 313. The web 16 includes at its inwardly curved center portion and at its lower edge a projection 320 for protection of the tongue In this embodiment, each carrying member of light-emitting means 12 of the device for unilateral or bilateral illumination of the oral cavity 10 (partially illustrated in FIGS. 9a-9c) is inserted into the back wall of the arch-shaped body 300, 301 near flange 312, 313, using the cavity formed by the front and back portions of said carrying member 12. Cable 18 of each carrying member 12 extends on the inner surface toward the front wall of the arch-shaped body 300, 301, to be held and fixed to this front side wall by means of holder 9.

Once clips 9 and cable 18 are set in their positions, the cheek retractor is placed in the mouth of the patient. Connector 22 is connected to second entry connection 58 to establish the power supply connection of illumination control system 14 and the feed source regulator of electric power 16 is connected to the first current entry connection 57. Once the electrical connection of carrying members 12, illumination control system 14 and feed source 16 is established, light-emitting means 20 will light and the dentist can regulate the intensity of each light-emitting means for unilateral or bilateral illumination of the patient's oral cavity. Moreover, once the electric current begins to flow toward illumination control system 14, charge sensor 25 of recharge circuit 24 contained in illumination control system 14 detects the level of charge of batteries 52 and instructs commutator 26 to allow the flow of electricity and thus recharge batteries 52 if they are discharged. In a preferred embodiment, said circuit commutator 26 allows operation of the device for unilateral or bilateral illumination of the invention only when batteries 52 are doing without the feed source regulator of electric power 16. Nevertheless, if the feed source regulator of electric power 16 is connected at that time, it will automatically work with the current that this provides, and batteries 52 will also be recharged at the same time.

Having previously described the use of the device for unilateral or bilateral illumination of the oral cavity of the invention in commercially available cheek retractors, it is possible for the carrying members of light-emitting means to be an integral part of the arched structures of the cheek retractor and to be connected by means of an electrically conductive element absorbed in and extending from the pair of arched structures and the arched elastic arm that connects these arched structures toward a connect/release member. The connect/release member can be located in the middle part of the arched elastic arm where said connect/release member serves to connect the illumination control system to the carrying members of light-emitting means.

We will now make reference to FIGS. 10*a*-10*c*. FIG. 10*a* shows a bite block especially designed for placement of the device for illumination of the oral cavity of the present invention. Preferably, the device for illumination of the oral cavity (partially shown in FIGS. 10*a*-10*c*) includes just one carrying member of light-emitting means 12, and the illumination control system 14 comprises a single potentiometer 50 to control light-emitting means 20 of carrying member 12 so the intensity of the light of light-emitting means 20 can be increased or decreased.

Bite block 500 has a main body 501 that has a side going toward the inside of the mouth 502, a side going toward the users gums 503 and a pair of opposed bite sides 504 located between the side that goes toward the inside of the mouth 502 and the side that goes toward the user's gums 503. The main body also includes a front side and a back side. Typically, the main body 501 of bite block 500 includes a bite portion 505 formed on each bite side 504 wherein bite portion 505 is the portion of bite block 500 where the user's upper and lower molars (not shown) will be supported when the bite block 500 is placed in position for use. As may be observed in FIG. 10*a*, bite portions 505 consist of a pair of walls that extend in a convergent way from the back side toward the front side of main body 501 wherein each wall of bite portion 505 includes transversely formed projections 560 to prevent slipping or sliding of the upper and lower molars on the surface of bite portion 505 when bite block 500 is in use. The angle of convergence of bite portions 505 will be dictated by the optimal opening angle of the mouth to keep the buccal cavity comfortably open during treatment or review. Moreover, the walls of bite portion 505 are joined in the front side of the main body by means of a reinforcing portion 511 that is resistant to the compression forces that the molars exert by means of the patient's jaws.

Main body 501 includes an outer wall 506 that covers main body 501 in its entirety on the side going toward the user's gums 503. Outer wall 506 extends perpendicularly beyond bite sides 504 of main body 501 in a such way that a pair of fin portions 507 are formed that stand out from the side that goes toward the respective user's gums. Preferably, bite block 500 also has an inner wall 508 located in the side that goes toward the inside of the user's mouth 502. Inner wall 508 extends perpendicularly toward the outside on bite sides 504. In general, inner wall 508 extends slightly toward the outside of bite portions 505 in order to form a pair of flange portions 509. In a preferred embodiment, the pair of fin portions 507 and the pair of flange portions 509 serve to form a retaining member to impede the lateral movement of the teeth when it is placed in bite block 500 in the user.

Returning again to FIG. 10*a*, bite block 500 in accordance with the present invention comprises a cavity 519 in main body 501 that it is defined by the inner walls of bite portions 505 as well as reinforcement portion 511. In a particularly preferred embodiment of the invention, cavity 519 includes an intermediate wall 550 that divides cavity 519 into a lower housing 521 and upper housing 520. Lower housing 521 of cavity 519 of main body 501 has as its object placing and fixing the attaching member (not shown) of the carrying member of light-emitting means 12 of the device 10 for unilateral illumination of the oral cavity in accordance with the principles of the present invention. The intermediate wall in combination with the inner walls of bite portions 505 and reinforcement portion 511 of upper housing 520 of the main body of bite block 500 define a surface for receiving and immobilizing the carrying member of light-emitting means 12 of the device 10 for unilateral illumination of the oral cavity (see FIG. 10*b*). Therefore, the dimensions of cavity 519 will be dictated by the dimensions that are established for device 10 for unilateral illumination of the oral cavity.

As can be seen in FIGS. 10*a*, 10*c*, reinforcement portion 511 of main body 501 includes a reduced portion in channel form 530 that extends from the side that goes toward the inside of the mouth toward outer wall 506 toward the front side of this reinforcement portion 511. Moreover, outer wall 506 also includes a reduced portion in channel form 532 that should be complementary with reduced portion 530, which extends on the side that goes toward the user's gums 503 from the front side toward the back side of the bite block. Channels 530, 532 form a path for placing and conducting cable 18 of the carrying member of light-emitting means 12 from the side that goes toward the inside of the mouth 502 toward the side that goes toward the user's gums 503, and finally leaving the mouth and connecting to the illumination control system 14 (not shown) of the illumination device 10 for increasing or reducing the intensity of the light of the light-emitting means 20.

Although the invention has been described by means of the foregoing detailed description with respect to preferred embodiments, it will be understood by those skilled in the art that several changes can be made without deviating from the spirit and scope of the invention.

The invention claimed is:

1. A device for illumination of the oral cavity that comprises:
    light-emitting means to unilaterally or bilaterally illuminate the oral cavity;
    a pair of carrying members of light-emitting means to house and establish electric power supply to light-emitting means and keep them in fixed position;
    an illumination control system to supply electric power and to regulate an exit current that feeds the light-emitting means to unilaterally or bilaterally illuminate the oral cavity and to control the intensity of light emitted by each pair of the carrying members of the light-emitting means in an independent way,
    means to connect the carrying members of the light-emitting means to the illumination control system; and
    a feed source regulator of the electric power;
    wherein the control of the intensity of illumination of the light-emitting means is obtained by means of potentiometers, each potentiometer controls a pair of light-emitting means to increase the intensity of the light of both light-emitting means, or increase the intensity of light of one light-emitting means alone and/or diminish the intensity of the other one, and wherein the illumination control system also includes a control circuit that has a feed entry of 6 to 12 volts; a diode D1 that protects the circuit against the polarity of the feed current; a resistor R5 that reduces the feed voltage supply to a light-emitting diode that indicates that the circuit is receiving electricity; the feed voltage is forked to be supplied to transistors T1, T2, where each transistor regulates the entry voltage and reduces it to 5 volts; the reduced voltage is driven toward corresponding resistors R2, R1 that reduces the voltage further from 5 volts to 3 volts to prevent heating of the light-emitting means connected to respective channels Ch1, Ch2; the reduced voltage that leaves R2, R1 is supplied to corresponding potentiometers POT1, POT2 to regulate the exit voltage in each channel Ch1, Ch2, and in this way also regulates the intensity of the light of each light-emitting means of the illumination control circuit; and wherein the illumination control circuit also contains respective grounded resistors R4, R3 to achieve the complete turning off of each light-emitting means connected to channels Ch1, Ch2, respectively; and diodes D2, D3 that serve as protection against the polarity of each channel Ch1, Ch2.

2. A bite block comprising:

a main body having a front side, a back side, a side facing to the inside of a user's mouth, a side facing to a user's gums and a pair of opposed bite sides located between the side facing to the inside of the user's mouth and the side facing to the user's gums;

a bite portion formed on each bite side to support the user's upper and lower molars when the bite block is placed in its position of use; said bite portions are formed by a pair of walls that extend in a convergent way from the back side toward the front side of the main body; and each wall of the bite portion includes transverse projections that impede slipping or sliding of the upper and lower molars on the surface of the bite portion;

a reinforcement portion located in the front side of the main body and that joins the walls of the bite portion, the reinforcing portion being resistant to the compression forces that the molars exert by means of the patient's jaws;

an outer wall covering the main body in its entirety on the side facing to the user's gums; the outer wall extends perpendicularly toward the outside to form a pair of fin portions that stand out from the side facing to the user's gums;

an inner wall located in the side facing to the inside of the user's mouth, this inner wall extending perpendicularly toward the outside on the bite sides to form a pair of flange portions;

wherein the bite block includes a cavity in the main body defined by inner walls of the bite portions as well as the reinforcement portion; each cavity includes an intermediate wall that divides the cavity into a lower housing and an upper housing;

wherein the lower housing of the cavity of the main body receives in a fixed way into its interior a holding member of a device for unilateral illumination of the oral cavity, wherein the illumination device includes light-emitting means to unilaterally illuminate the oral cavity; one carrying member of the light-emitting means to house and establish the electric power supply to the light-emitting means and keep them in a fixed position; an illumination control system to supply electric power and regulate exit current that feed the light-emitting means to illuminate the oral cavity and to control the intensity of light emitted by the light-emitting means; means to connect the carrying member of the light-emitting means to the illumination control system; and a feed source regulator of the electric power;

the intermediate wall in combination with the inner walls of the bite portions and the reinforcement portion of the upper housing of the main body of the bite block define a surface for receiving and immobilizing the carrying member of the light-emitting means of the device for unilateral illumination of the oral cavity; and a channel formed in the reinforcement portion and the outer wall to place and conduct a cable of regulated power supply to the carrying member of the light-emitting means from the side facing to the interior of the mouth toward the side facing to the user's gums, finally leaving the mouth and being connected to the illumination control system of the illumination device to increase or reduce the intensity of the light of the light-emitting means unilaterally.

* * * * *